US00PP09535P

United States Patent [19]

Trees

[11] Patent Number: Plant 9,535

[45] Date of Patent: Apr. 30, 1996

[54] GERANIUM PLANT NAMED 'BFP-901 BRIGHT RED'

[75] Inventor: Scott C. Trees, Arroyo Grande, Calif.

[73] Assignee: Geo. J. Ball, Inc., West Chicago, Ill.

[21] Appl. No.: 432,271

[22] Filed: May 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

A new and distinct *Pelargonium×hortorum* cultivar named 'BFP-901 Bright Red' is provided. This new Zonal Geranium cultivar was the result of a controlled breeding program wherein a plant designated 3804-1 (non-patented in the United States) was pollinated by the 'Fox' cultivar (U.S. Plant Pat. No. 7,083). The new cultivar forms attractive semi-double bright red florets in a freely flowering display. Attractive dark green foliage with zonation is well retained during shipment. The growth habit is self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-901 Bright Red'.

The new cultivar is a product of a planned breeding program which had the objective of the creation of a new Geranium cultivar that exhibits uniform flowers, dark green foliage, a medium of self-branching growth habit that requires no growth regulator, a propensity for rapid rooting, and a stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 3804-1 (non-patented in the United States) which exhibits single scarlet florets with dark green foliage. The male parent (i.e., pollen parent) was the 'Fox' cultivar (U.S. Plant Pat. No. 7,083) which exhibits semi-double purple florets with medium green foliage. The parentage of the new 'BFP-901 Bright Red' cultivar can be summarized as follows:

3804-1×'Fox'.

The 'BFP-901 Bright Red' cultivar was discovered and selected during 1992 as a highly distinctive flowering plant from among the pogeny of the stated cross at Arroyo Grande, Calif., U.S.A. This plant was initially designated BFP-901.

It was found that the new cultivar of the present invention:

(a) exhibits attractive semi-double bright red florets in a freely flowering display, (b) forms attractive dark green foliage with zonation, and (c) exhibits a medium self-branching growth habit in the absence of a growth regulator.

When plant material of the 'BFP-901 Bright Red' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-901 Bright Red' cultivar was accomplished when vegetative cuttings were taken from the initial selection in a controlled environment at Arroyo Grande, Calif., U.S.A., by a technician working under the direction and supervision of the originator of the new cultivar. Horitcultural examination of plants resulting from such asexual propagation during 1993 has demonstrated that the combination of characteristics as herein described for the 'BFP-901 Bright Red' cultivar is firmly fixed and is retained through successive generations of such reproduction.

The new 'BFP-901 Bright Red' cultivar has not been observed under all possible environmental conditions. Accordingly, the described phenotype may vary somewhat with variations in the environment, such as temperature, light intensity, and day length.

Of the many commercial cultivars, 'BFP-420 Bright Red' cultivar (U.S. Plant patent application Ser. No. 341,912, filed Nov. 15, 1994) is considered to be the most similar to the new 'BFP-901 Bright Red' cultivar. When the new cultivar of the present invention is compared to the 'BFP-420 Bright Red' cultivar, it is found that the 'BFP-901 Bright Red' cultivar exhibits large umbels (e.g., approximately 9.6 to 10.5 cm. in diameter vs. approximately 7.5 to 8.5 cm.), and larger leaves (e.g., approximately 9.0 to 10.9 cm×approximately 7.0 to 9.0 vs. approximately 8.5 go 9.5 cm.×approximately 7.0 to 7.6 cm.).

The new cultivar of the present invention is being marketed by Geo. J. Ball, Inc. under the Showcase trademark.

BRIEF DESCRIPTION OF THE PHOTOGRAPH

The accompanying photograph of FIG. 1 shows a typical plant of the 'BFP-901 Bright Red' cultivar with colors generally being as nearly true as it is reasonably possible to make the same in color illustrations of this character. Fully-opened umbels together with the foliage are illustrated. The plant was being grown in a greenhouse at West Chicago, Ill., U.S.A.

DETAILED DESCRIPTION

Figure 1:
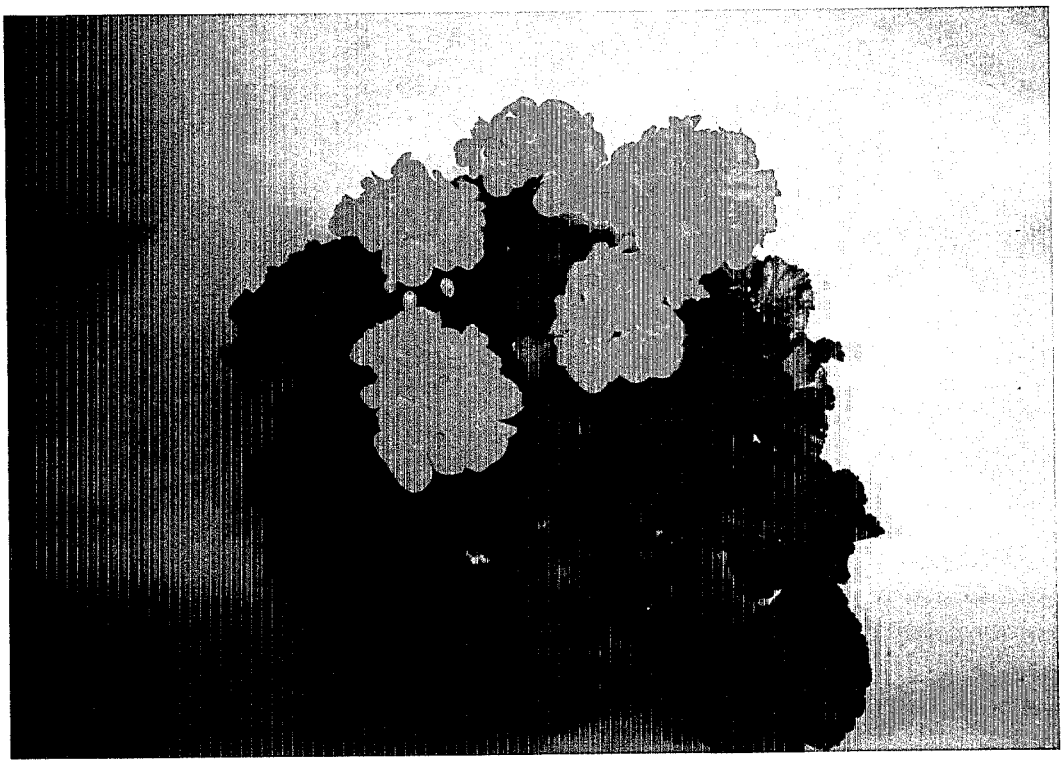

The following observations, measurements and comparisons describe plants grown in Ball FloraPlant's greenhouses at West Chicago, Ill., U.S.A. under greenhouse conditions which approximate those generally used in commercial practice. In the following description, color references are made to the R.H.S. Colour Chart of The Royal Horticultural Society, London, England. The color values were determined between 9:00 and 9:30 a.m. on Dec. 27, 1994, under natural light conditions of 2,000 footcandles.

Classification:

*Botanical.*—*Pelargonium×hortorum* Bailey, cv. 'BFP-901 Bright Red'.

*Commercial.*—Zonal Geranium.

INFLORESCENCE

A. Umbel:

*Average diameter.*—Approximately 9.6 to 10.5 cm. compared to approximately 7.5 to 8.5 cm. for the 'BFP-420 Bright Red' cultivar.

*Average depth.*—Approximately 6.0 to 9.5 cm. compared to approximately 5.0 to 7.0 cm. for the 'BFP-420 Bright Red' cultivar.

*Peduncle length.*—Approximately 13.0 to 19.0 cm. compared to approximately 13.5 to 18.0 cm. for the 'BFP-420 Bright Red' cultivar.

*Pedicel length.*—Approximately 2.8 to 3.0 cm. compared to approximately 2.4 to 2.7 cm. for the 'BFP-420 Bright Red' cultivar.

*Number of umbels plant.*—When grown in a 10 cm. pot at 9 weeks after the sticking of a rooted cutting, there commonly are 4 to 6 umbels per plant. This compares to approximately 3 to 6 umbels per plant for the 'BFP-420 Bright Red' cultivar.

*Number of florets umbel.*—When grown in a 10 cm. pot at 9 weeks after the sticking of a rooted cutting, there commonly are approximately 20 to 37 florets per umbel. This compares to approximately 30 to 36 florets per umbel for the 'BFP-420 Bright Red' cultivar.

B. Corolla:

*Average diameter.*—Approximately 4.0 to 4.6 cm. compared to approximately 4.1 to 4.4 cm. for the 'BFP-420 Bright Red' cultivar.

*Form.*—Both the 'BFP-901 Bright Red' cultivar and the 'BFP-420 Bright Red' cultivar are semi-double with petaloids and commonly each form approximately 5 to 6 petals per floret.

*Number of petaloids.*—Commonly approximately 1 to 4 petaloids are formed per floret. This compares to approximately 2 to 3 petaloids per floret for the 'BFP-420 Bright Red' cultivar.

*Color.*—General tonality from a distance of three meters: Red. Adaxial: Red Group 46B. This compares to Red Group 44B for the 'BFP-420 Bright Red' cultivar. Abaxial: Red Group 46C. This compares to Red Group 43B for the 'BFP-420 Bright Red' cultivar.

C. Bud:

*Shape.*—Oval-rounded.

*Color.*—Adaxial: Red Group 46B compared to Red Group 44B for the 'BFP-420 Bright Red' cultivar. Abaxial: Red Group 46C compared to Red Group 43B for the 'BFP-420 Bright Red' cultivar.

D. Reproductive organs:

*Androecium.*—The anthers are commonly approximately 2.0 to 2.5 mm. in length. The pollen color for both the 'BFP-901 Bright Red∞ cultivar and the 'BFP-420 Bright Red' cultivar is Orange-Red Group 31A. The filaments commonly are approximately 11 to 12 mm. in length.

*Gynoecium.*—The pistil length commonly is approximately 10 mm. There is a single stigma which commonly has a length of approximately 5 mm. which commonly branches into 5 parts, and, the style length commonly is approximately 5 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming.

G. Durability: Ships well.

PLANT

A. Foliage: Dark green with zonation.

*Form.*—Reniform, with cordate base.

*Margin.*—Crenate.

*Color.*—Adaxial: Yellow-Green Group 147A with a zone of Yellow-Green Group 146A for both the 'BFP-901 Bright Red' cultivar and the 'BFP-420 Bright Red' cultivar. Abaxial: Yellow-Green Group 147B for both the 'BFP-901 Bright Red' cultivar and the 'BFP-420 Bright Red' cultivar.

*Size.*—Approximately 9.0 to 10.9 cm. at the widest point and approximately 7.0 to 9.0 cm. at the narrowest point. This compares to approximately 8.5 to 9.5 cm. at the widest point and approximately 7.0 to 7.6 cm. at the narrowest point for the 'BFP-420 Bright Red' cultivar. A medium self-branching growth habit is exhibited in the absence of the use of a growth regulator.

B. General appearance and form:

*Internode length.*—Commonly varies from approximately 1.0 to 2.5 cm. This compares to approximately 2.0 to 2.5 cm. for the 'BFP-420 Bright Red' cultivar.

*Branching pattern.*—Freely basal branching. No pinching is required to obtain self-branching. A medium self-branching growth habit is exhibited in the absence of the use of a growth regulator.

*Height.*—Approximately 26 to 32 cm. above a 10 cm. pot at 9 weeks under standard greenhouse conditions.

I claim:

1. A new and distinct Geranium plant named 'BFP-901 Bright Red', substantially as herein shown and described, which:

(a) exhibits attractive semi-double bright red florets in a freely flowering display, (b) forms attractive dark green foliage with zonation, and (c) exhibits a medium self-branching growth habit in the absence of a growth regulator.

* * * * *